United States Patent [19]
Mignot et al.

[11] Patent Number: 5,422,250
[45] Date of Patent: Jun. 6, 1995

[54] PROCESS FOR THE PREPARATION OF HUMAN FACTOR VIII AND ANALOGS OF FACTOR VIII

[75] Inventors: Gérard Mignot, Gif S/Yvette; Nicholas Bihoreau, Palaiseau; Philippe Adamowicz, Vaucresson, all of France

[73] Assignee: TM Innovation, Lyons, France

[21] Appl. No.: 970,951

[22] Filed: Nov. 3, 1992

Related U.S. Application Data

[63] Continuation of Ser. No. 650,580, Feb. 4, 1991, abandoned.

[30] Foreign Application Priority Data

Feb. 5, 1990 [FR] France ................... 90 01302

[51] Int. Cl.$^6$ .................. C12N 5/06; C12N 5/10; C12N 9/50
[52] U.S. Cl. .................. 435/69.6; 435/240.2; 435/240.3; 935/34
[58] Field of Search ............ 435/69.6, 70.3, 212, 435/240.2, 240.3, 240.31; 935/33, 34; 424/94.64

[56] References Cited

U.S. PATENT DOCUMENTS

| Re. 29,698 | 7/1978 | Fekette et al. ........... 530/383 |
| 4,443,546 | 4/1984 | Stemerman et al. ........ 435/240.31 |
| 4,670,394 | 6/1987 | Pollard et al. ........... 435/70.3 |
| 4,965,199 | 10/1990 | Capon et al. ........... 435/240.2 |
| 4,980,456 | 12/1990 | Scandella et al. ........... 435/69.6 |
| 5,112,950 | 5/1992 | Meulien et al. ........... 435/69.6 |
| 5,132,223 | 7/1992 | Levine et al. ........... 435/240.3 |
| 5,147,790 | 9/1992 | Wilson ........... 435/70.3 |
| 5,171,844 | 12/1992 | Van Ooyen et al. ........... 435/69.6 |
| 5,198,349 | 3/1993 | Kaufman ........... 435/69.6 |

FOREIGN PATENT DOCUMENTS

| 0053046 | 2/1982 | European Pat. Off. ...... A61K 35/16 |
| 0098256 | 1/1984 | European Pat. Off. ...... C07G 7/00 |
| 0254076 | 1/1988 | European Pat. Off. ...... C12N 15/00 |
| 0306968 | 3/1989 | European Pat. Off. ...... C12N 15/00 |
| 8605190 | 9/1986 | WIPO ...................... C07K 3/24 |

OTHER PUBLICATIONS

S. C. Thornton et al., Science 222:623–625, 11 Nov. 1983.

B. J. Ballermann, American Journal of Physiology 256: C182–C189, Jan. 1989.

M. Windholz et al., The Merck Index, 10th Edition, 1983, Monographs 2915 and 4543 at pp. 427 and 672–673.

P. Meulien et al., Protein Eng 2: 301–306, 1988, abstracted in Biological Abstracts 86(6): AB-75–76, Ref. No. 55328, Mar. 1989.

Primary Examiner—Stephen G. Walsh
Attorney, Agent, or Firm—Blakely, Sokoloff, Taylor & Zafman

[57] ABSTRACT

The present invention relates to a process for the preparation of factor VIII or an analog of factor VIII by culture, in a Culture medium, of cells which produce said factor VIII or analog of factor VIII and the separation of factor VIII or its analog, wherein the culture medium contains at least one derivative of a polycationic and/or polyanionic polymer.

It also relates to factor VIII or analog of factor VIII and to the complex of factor VIII or analog of factor VIII with a derivative of a polycationic and/or polyanionic polymer obtained by using this process.

4 Claims, 2 Drawing Sheets

PROCESS FOR THE PREPARATION OF HUMAN FACTOR VIII AND ANALOGS OF FACTOR VIII

This is a continuation of application Ser. No. 07/650,580, filed Feb. 4, 1991, now abandoned.

The present invention relates to a process for the preparation of human factor VIII and analogs of factor VIII.

Factor VIII is a blood coagulating factor which is used in the treatment of patients suffering from hemophilia A.

The factor VIII which is used in this treatment is at present essentially composed of concentrates of factor VIII obtained from human plasma by fractionation. Since then, attempts have been made to replace this source of factor VIII by a source more easily accessible and less susceptible to virus or other contaminations, thus, great effort has been made in order to obtain factor VIII by genetic engineering. The results presently obtained show that recombinant factor VIII exhibits all the characteristics of natural factor VIII and that it can be obtained under satisfactory industrial conditions.

The preparation of factor VIII by processes employing genetic engineering techniques have already been widely described notably in the following patents:

EP-A-162,067,
EP-A-182,448,
EP-A-150,735,
EP-A-157,556 and
EP-A-160,457.

In particular, the Patent EP-A-162,067 mentions the expression of factor VIII in various types of eukaryotic cells, particularly CHO cells.

The Patent EP-A-160,457 also describes the expression of factor VIII in eukaryotic cells, particularly BHK cells and also, vertebrate cells from cell lines such as VERO, HeLA, CHO, WI38, COS-7 and MDCK may be used.

The Patents FR-A-86/08,258 and FR-A-87/04,699 describe the preparation of factor VIII using eukaryotic cells and vaccinia virus as an expression system. In order to obtain an optimum production of factor VIII, the culture medium contains von Willebrand factor.

By way of eukaryotic cells, the Patent EP-A-253,455 also suggests the use of yeasts for preparing factor VIII.

Several analogs of factor VIII have also been proposed. Among the patents covering these derivatives, the following can particularly be mentioned:

WO-A-86/06,101,
EP-A-232,112,
WO-A-87/07,144,
WO-A-88/00,381,
EP-A-265,778,
EP-A-294,910 and
EP-A-303,540.

These analogs of factor VIII exhibit various advantages over "natural factor VIII" and, like it, can be obtained by genetic engineering techniques.

The processes which are used at present preferably employ eukaryotic cells which express factor VIII, these being either cells which have integrated one or more coding sequences for factor VIII in the chromosome, or cells which incorporate virus vectors that express factor VIII.

This type of technology is extensively described in the aforementioned patents and will not be redescribed here in detail. Mention will simply be made of cells which express factor VIII or an analog of factor VIII.

By analog of factor VIII, there is understood a molecule which has the activity of factor VIII and which is obtained from factor VIII by deletion of some amino acids or a molecule of factor VIII which has undergone certain potential mutations but which nevertheless retains the principal activity of factor VIII.

As described in the Patents WO-87/04,187, FR-A-8,608,258 and FR-A-87/04,699, it may be useful, in order to optimize the preparation of factor VIII or of an analog of factor VIII, to envisage the addition into the cell culture medium of von Willebrand factor or of phospholipid.

It has in effect been shown that the presence of this von Willebrand factor in the culture medium made it possible to stabilize factor VIII and to considerably improve the yield.

For similar reasons to those that have just been mentioned, the von Willebrand factor used is obviously a recombinant von Willebrand factor in order to avoid any risk of contamination. This requires the use of an additional step in the production and an increase in the cost of the process for the preparation of factor VIII, notably, a doubling of the price.

It will therefore be useful to have a process for the preparation of factor VIII which does not require the use of von Willebrand factor but which nevertheless results in high yields of factor VIII.

The aim of the present invention is precisely to propose a solution to this problem.

More particularly, the present invention relates to a process for the preparation of factor VIII or an analog of factor VIII by culture, in a culture medium, of cells which produce said factor VIII or analog of factor VIII and the separation of factor VIII or its analog, wherein the culture medium contains at least one derivative of a polycationic and/or polyanionic polymer.

Among the analogs of factor VIII, mention can be made particularly of factor VIII delta 2 which corresponds to a deletion of amino acids 771 to 1666 of factor VIII and whose preparation is more particularly described in the Patent EP 303,540.

Patent EP 0,303,540 relates to the factor VIII analog in which amino acids 771 to 1666 have been deleted. It will also be referred to throughout the description and the examples as FVIIIΔII.

The factor VIII analog according to Patent EP 0,303,540 is preferably prepared from a culture of eukaryotic cells that produce the said analog on a suitable culture medium, and the factor VIII obtained is separated.

The cells have preferably have been infected with a recombinant viral vector such as vaccinia virus, which provides the expression of the cDNA of the factor VIII analog in the cells. The latter are preferably BHK21 cells.

However, it is also possible to transfect the cells with an integration vector containing the cDNA of the factor VIII analog, surrounded by the elements necessary for its expression in eukaryotic cells and a DNA segment that promotes the integration of the vector in the cellular DNA.

In this case, the cDNA coding for the factor VIII analog is preferably inserted in front of a gene coding for a selection marker, to give a bicistronic transcription product.

The polymers in accordance with the present invention are preferably derivatives of polyosidic polymers notably polysaccharides.

These polymers are preferably sulfated.

This type of polymer is known, they are especially products obtained by bacterial fermentation, for example, dextran, or they are extraction products such as mucopolysaccharides of the type heparin, heparin of low molecular weight or heparinoids, or dermatan sulfate or heparan sulfate.

Hydroxyethylstarch sulfate can also be used by way of polymer.

These compounds are particularly useful in view of their low cost and their availability.

The polymer used in accordance with the present invention has a molecular weight between 1000 and 1,000,000.

According to a particular embodiment of the invention, the polymer used is a sulfated dextran. The degree of sulfation of this sulfated dextran is of the order of 0.5% to about 18% by weight of sulfur and preferably from 10 to about 18%.

Sulfated dextrans of very diverse molecular weight can be used in accordance with the invention. Their weight can thus vary from 5000 to 700,000 Daltons.

Using an advantageous embodiment of the invention, the polymer derivative which can be used is coupled with a divalent metallic ion. The following ions can be mentioned, in a non-restrictive manner, $Ca^{2+}$, $Mg^{2+}$, $Mn^{2+}$, $Cu^{2+}$, the $Ca^{2+}$ ions being preferred.

The presence of a polycationic and/or polyanionic polymer, in accordance with the invention, in a culture medium which is suitable for the production of factor VIII or analog of factor VIII and exempt of von Willebrand factor, results in yields of factor VIII or analogs of factor VIII which are significantly higher than those obtained in a medium containing neither von Willebrand factor nor a polymer in accordance with the invention.

Thus, it emerges from the experiments carried out in accordance with the process of the present invention and which are described in the examples below, that it is possible, using a culture medium containing sulfated dextran of a molecular weight of 500,000, to obtain large quantities of factor VIII delta 2 determined by two different methods, one based on an immuno-enzymatic method, using anti-factor VIII monoclonal antibodies, and the other by a physico-chemical method such as PAGE-SDS analysis under reducing or non-reducing conditions, which reveals a major band at 165 KDa which represents the major form of factor VIII delta 2 expressed in the absence of bovine serum.

Molecular weights (5000, 8000, 15,000, 50,000, 500,000 Da) gave essentially equivalent results for the expression of factor VIII.

The culture medium, supplemented with a polycationic and/or polyanionic polymer, may naturally contain other agents which are likely to favor the production of factor VIII. They may be antiprotease agents and/or calcium chloride known for its stabilizing properties.

Under these conditions, it has been shown, for a culture medium supplemented with 1000 mg/l of sulfated dextran and 2 mmoles of calcium chloride (1 mM in the minimal medium+1 mM added), that it is possible to accumulate in 24 hours, quantities of factor VIII delta 2, measured by an immuno-enzymatic method, which are 6 to 7 times higher than the quantity accumulated in the absence of exogenous von Willebrand factor.

The molecule of factor VIII, complete or deleted in the B region, has the characteristic of possessing high densities of very localized charges which create positively and negatively charged poles capable of binding to Coulomb forces (ionic type interactions) to polyanions and polycations respectively. The beneficial effect of sulfated dextran on the production of factor VIII can be explained by the existence of such interactions between the sulfate groups of dextran and the basic amino acids of factor VIII. This stabilization of the complete or deleted molecule of factor VIII is furthermore to be associated with an increase in the rate of expression of factor VIII or derivative of factor VIII.

There is probably formation of a complex between the complete or deleted molecule of factor VIII and at least one of the molecules of the polycationic and/or polyanionic derivative employed in the culture medium.

The present invention also relates to this complexed form of factor VIII or derivative of factor VIII.

This stabilized form of factor VIII or one of its derivatives can exhibit great usefulness in particular for the storage of said factor VIII or derivative of factor VIII during the production process or following it. Furthermore, when factor VIII or one of its derivatives is complexed with sulfated dextran which is a freeze-drying agent, it can be expected that the complex thus formed will also exhibit a good freeze-drying capacity.

The presence of sulfated dextran can therefore at the same time have a stabilizing effect towards factor VIII and also a stimulating effect on the expression of factor VIII through interaction at the level of cell membranes.

The culture medium used in accordance with the invention is preferably a culture medium without serum, derived especially from recombinant human insulin and which may contain other exogenous proteins.

These proteins are preferably used at a concentration of the order of 4 mg/l.

The cells used for the production of factor VIII or analog of factor VIII are preferably mammalian cells and more particularly recombinant CHO cells which express factor VIII or analog of factor VIII in a continuous manner.

These cells are transfected with an integration vector containing the cDNA of factor VIII or derivative of factor VIII in the presence of elements which are required for its expression in eukaryotic cells and a segment of DNA which favors integration of the vector in cellular DNA. It is thus possible to use by way of expression vector for factor VIII, pTG 1020, and for factor VIII delta 2, pTG 1509 which are described in the Patent EP 0,303,540 as well as expression vectors of similar construction. The strains for the plasmids pTG 1509 and pTG 1020 have been deposited under the No. I-679 and I-681 in the National Collection of Microbial Cultures.

The transfection of CHO cells with these integration vectors is carried out according to the technique described in Patent EP 0,303,540 as described below:

The following examples of the transfection of CHO cells with certain integration factors are taken from Patent EP 0,303,540.

Example A1

Construction of plasmids carrying derivatives of the cDNA of the factor VIII which have undergone deletion in the region corresponding to domain B.

The starting plasmid is plasmid pTG1080 which carries the cDNA of factor VIII, nucleotides −64 to 8230, cloned into the SalI site of pUC8 (this plasmid has been described in French Patent 86/08,258).

From this plasmid, 2 derivatives were prepared, one (ΔI) comprising a deletion in domain B corresponding to amino acids 868 to 1562, the other (ΔII) corresponding to a deletion of amino acids 771 to 1666.

The construction ΔII hence abolishes the cleavage site at position 1649.

a) Plasmid pTG1080 was digested with the enzyme PstI to release a 2.7-kb fragment comprising 5' end corresponding to nucleotides −64 to 2641 of the cDNA of factor VIII.

This PstI fragment was cloned into the vector pTG1-POLY (a cloning vector derived from pML2, containing an origin of replication which is active in *E. coli* and the β-lactamase gene, into which a polylinker possessing 12 single restriction sites has been inserted). This vector is identical to the vector pTG14 described in Patent PCT-FR 85/00,096, with the exception of the polylinker which replaces the HindIII linker. In this construction, the BglII site of the polylinker is adjacent to the PstI site (nucleotide 2641) of the FVIII sequence.

The 3'-position of the FVIII coding sequence (nucleotides 4801 to 8230) is then introduced into this BglII site, in the form of a BamHI fragment also isolated from pTG1080.

The construction possessing the two FVIII segments in the correction orientation is referred to as pTG1501. The factor VIII cDNA sequence carried by this construction is referred to as FVIIIΔI. The PstI/BglII/BamHI junction thereby formed preserves the FVIII reading frame.

b) From pTG1501, a KpnI-SphI fragment (corresponding to nucleotides 1811 to 6580) is recovered and introduced into the vector M13TG131, and nucleotides 2367 to 5056 are deleted from it by the so-called "loop out mutagenesis" technique with a synthetic oligonucleotide as set forth in EP 0,303,540.

The vector which has undergone deletion is referred to as M13TG1510; the FVIII cDNA sequence which has undergone deletion is referred to as FVIIIΔII. Sequencing analysis confirms that the sequence is correct.

Example A2

Expression of the FVIIIΔI and sequences by recombinant vaccinia viruses.

In French Patent 86/08,258, plasmid pTG1016, which carries the cDNA sequence of factor VIII downstream from the promoter of the gene coding for the 7.5K protein of the vaccinia virus, was described, and this expression block is inserted in the TK gene of vaccinia virus.

A derivative of plasmid pTG1016, pTG1030 (identical to the above except for the BglII-PstI deletion in the untranslated 5' region of the FVIII sequence) was used for integrated the constructions which have undergone deletions, FVIIIΔI and ΔII, in place of the native sequence, in the vector designed to permit integration in the vaccinia virus genome.

The BamHI-BglII fragment (corresponding to nucleotides 864 to 6056) of the native sequence of pTG1030 is excised and replaced by the BamHI-BglII fragment of pTG1501 (FVIIIΔI) to give pTG1506, or by the BamHI-BglII fragment of M13TG1510 (FVIIIΔI) to give pTG1507).

The DNA blocks, comprising the TK gene of vaccinia interrupted by the FVIIIΔ cDNA placed under the vaccinia 7.5 k promoter, are integrated in the vaccinia virus genome, by homologous recombination, according to the classical technique.

The corresponding recombinant viruses are referred to as VV.TG.FVIII1506 (FVIIIΔI) and VV.TG.FVIII1507 (FVIIIΔII).

The recombinant viruses are used for infecting BHK21 cell lawns ($2\times 10^6$ cells) with 1 pfu/cell. After 1 hour's adsorption, the cultures are washed and replenished with fresh medium without serum, to which 1% BSA and 1 mM $CaCl_2$ has been added. Samples of medium are withdrawn after 24 and 48 hours and assayed for the quantity of factor VIII present, determined by immunoradiometric assay (FVIII:Ag), and for the procoagulant activity of the factor VIII (FVIII:C).

The FVIII or FVIIIΔ antigen is assayed by sandwiching it between the immunoglobulin G of the inhibitory serum of a hemophilic patient, the immunoglobulin being adsorbed on the wall of the test tube, and a radioactive anti-factor VIII monoclonal antibody specific for an epitope of the light chain, according to a method described by Lee et al.

The measurement of the factor VIII activity (FVIII:C) is carried out in the classical manner by means of the activated particle thromboplastin time (APTT).

The results are presented in the following table.

TABLE A1

Determination of the quantity of FVIII:Ag and of the FVIII:C procoagulant activity in the supernatant of BHK21 cultures infected with recombinant VV viruses (results expressed in mU/mL — threshold of detection = 1 mU/mL).

| Recombinant VV | 24 hours | | 48 hours | |
|---|---|---|---|---|
| | FVIII:C | FVIII:Ag | FVIII:C | FVIII:Ag |
| VV.TG.1030 (FVIII) | 47.5 | 78.5 | 42.5 | 120.0 |
| VV.TG.1506-9 (FVIIIΔI) | 110.0 | 128.0 | 155.0 | 187.5 |
| VV.TG.1507-6 (FVIIIΔII) | 160.0 | 486.7 | 548.0 | 615.0 |

The results show that the two molecules which have undergone deletion are biologically active in a blood coagulation test, and that a larger quantity of protein is obtained with FVIIIΔ constructions that with the intact FVIII (2-times increase with FVIIIΔI and 5-times increase with FVIIIΔII).

In addition, the FVIII:C activity does not fall between 24 and 48 hours, whereas it falls with the intact molecule. It is known that the latter has to be stabilized with the von Willebrand factor in order to retain its activity (French Patent 86/08,258).

Example A3

Establishment of cell lines that express factor VIII or factor VIIIΔII.

1) Construction of plasmids

The coding sequences for factor VIII and for factor VIIIΔII were introduced into a vector, pTG384, designed for promoting its integration in the genome of mammalian cells in multicopy form. This vector has been described in French Patent 86/09,043. The important elements of this vector are:

a) a murine mitochondrial DNA segment which promotes the integration of exogenous DNA sequences in the form of several copies in tandem.

b) an expression cassette comprising the enhancer (transcription activative) sequences of SV40 (72-bp repeat sequence), the major late promoter (MLP) of adenovirus 2, and the gene coding for the XGPRT (xanthine:guanine phosphoribosyltransferase) selection marker. The vector is designed to enable a selected cDNA to be inserted on the 5' side of the XGPRT gene, so as to obtain a bicistronic transcription product. The vector also comprises, on the 3' side of the XGPRT, the intron of the small t antigen of SV40 and its polyadenylation sequences.

c) The origin of replication provides for the propagation of the vector E. coli.

The coding sequences for FVIII were inserted in the vector pTG384, in the single HindIII site (upstream from the XGPRT gene). The ends liberated by the HindIII digestion are made blunt by treatment with the Klenow fragment of DNA polymerase I.

The complete FVIII sequence is recovered from plasmid pTG1080 (see Example 1) in the form of an SmaI-HpaI fragment (the SmaI site is situated in the polylinker upstream from the initiator ATG, and the HpaI site is situated at nucleotide 7,434). The ligation of this fragment in the vector pTG384, opened with HindIII and treated with Klenow, gives plasmid pTG1020.

To perform the analogous construction with the factor VIII gene which has undergone deletion, the BamHI-BglI fragment (nucleotides 1864 and 6050 of FVIII) is exchanged, in pTG1020, with the FVIIIΔII fragment, BamHI-BglI of M13TG1510, according to the same principle as for the construction of pTG1507. The vector pTG304 which has inserted FVIIIΔII is referred to as pTG1507.

2) Transfection of CHO cells with plasmids pTG1020 and pTG1509.

Lawns of CHO cells were transfected with the DNA of plasmids pTG1020 (FVIII) or pTG1509 (FVIIIΔII) by the calcium phosphate precipitate method, with 5 or 10 μg of DNA per dish 8.5 cm in diameter. 48 hours after the transfection, the cells are trypsinized, diluted and inoculated in MFMΔ2000 selective medium supplemented with hypoxanthine (15 mg/L), thymidine (10 mg/L), xanthine (250 mg/l) aminopterin (0.2 mf/L), mycophenolic acid (25 mg/L) and 10% of dialized foetal calf serum.

After two weeks, the clones of cells resistant to selective medium are removed and cultured in 1-ml and then 2-ml cups. When the cells reach 70% confluence, the medium is removed and the cell lawns are washed and replenished with fresh medium containing 5% of inactivated serum (to avoid a high background in the coagulation tests).

After 24 hours, the medium is harvested and analyzed for the presence (FVIII:Ag) and the activity (FVIII:C) of factor VIII.

Several clones were obtained. In the first analysis, most of the clones that express complete FVIII are seen to produce less material than the clones that express factor VIIIΔII.

Two clones were selected:

CHO-TG1020-22-12 which expresses complete FVIII and CHOTG-1509-18, which expresses FVIII-ΔII.

The levels of FVIII expression and activity are presented in the following table:

TABLE A2

Determination of FVIII:Ag and o FVIII:C (in mU) in the supernatant of CHO clones ($10^6$ cells), harvested after 24 hours.

| | FVIII:Ag | FVIII:C |
|---|---|---|
| CHO-TG1020-22-12 | 63 | 60 |
| VHO-TG1509-18 | 504 | 500 |

A production of factor VIIIΔII 10 times greater than that of the complete factor VIII is observed, which confirms the results observed in the vaccinia model.

Example A4

Activation by thrombin of the various native and recombinant factor VIII molecules.

Different factor VIII molecules were compared in a study of kinetics of activation by thrombin: native factor VIII derived from plasma and the recombinant factor VIII, complete and ΔII, expressed in the CHO clones.

The activation is measured in a classical coagulation test (APTT) after incubation in the presence of a catalytic amount of thrombin.

The recombinant FVIII and the plasma FVIII are activated in the same manner (by a factor of 20) and according to very similar kinetics. The FVIIIΔII is activated much more strongly (by a factor of 80 after 5 minutes incubation with thrombin).

Although the factor VIIIΔI is much more strongly activated, it is not activated more rapidly than the other two molecules (in contrast to what has been observed by others with the factor VIII constructions), thereby showing that factor VIIIΔII is not preactivated, which is important for the purpose of its therapeutic use.

The fact that FVIIIΔII is not preactivated is confirmed by the good correlation between the FVIII:Ag and FVIII:C levels, both in the vaccinia model and in CHO lines.

The process according to the present invention therefore exhibits several advantages.

It allows factor VIII or an analog of factor VIII to be obtained by genetic engineering with an optimized yield.

It does not require the presence of von Willebrand factor in the culture medium and thus lead to a significant gain in time and in cost for the industrial production of factor VIII or analog of factor VIII.

Finally, the type of polymer used in accordance with the invention does not carry any risk of virus or other contamination, it is not very costly, and it is easy to obtain for the specialist.

The present invention also relates to factor VIII or analog of factor VIII obtained according to the process of the invention.

Other advantages and characteristics of the present invention will emerge from the non-restrictive examples thereof given below.

EXPERIMENTAL SECTION

Figure 1:
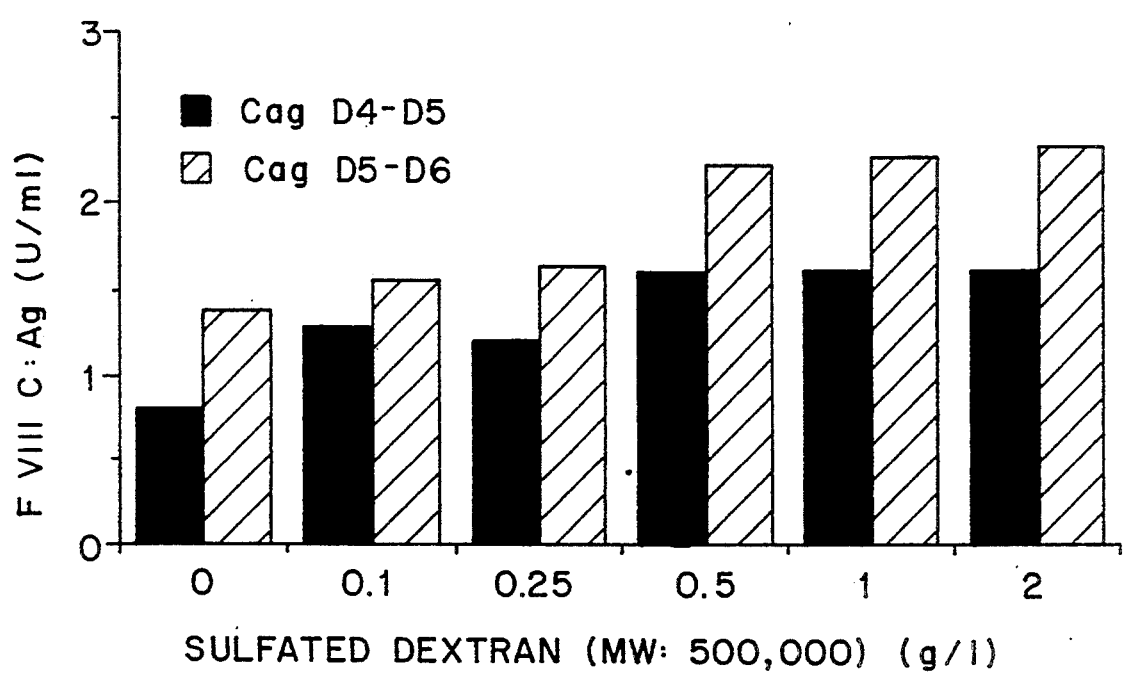
FIG. 1 shows the dose effect of sulfated dextran on the expression of factor VIII.

Studies of the effect of sulfated polyosidic polymers on the expression of factor VIII delta 2 were carried out using the clone CHO TG2307-11.

EXAMPLE 1

Study of the Effects of Dextran T 2000 on the Expression of Factor VIII Delta 2

In a first step, by way of reference, the effects of dextran T 2000 (PHARMACIA MW : 2,000,000 Da) were evaluated. Table 1 below summarizes the results obtained in comparison with a medium containing 2 U/ml of recombinant von Willebrand factor.

Dextran T 2000 (non-sulfated) has little effect on the expression of factor VIII delta 2 in the absence of serum and recombinant von Willebrand factor.

Consequently, the dextran matrix consisting of non-substituted glucopyranosyl units do not interfere with the molecule of factor VIII delta 2.

TABLE I

STUDY OF THE EFFECTS OF THE ADDITION OF DEXTRAN T 2000 PRODUCTION MEDIA FOR FACTOR VIII DELTA 2 CLONE CHO TG 2307-11-3

| PRODUCTION MEDIA | APTT mU/ML D3–D4 | AVERAGE |
|---|---|---|
| H/I HUM INS 4 mg/L + 2 U vWFrec 2 U/ml vFW | 1000 1000 | 1000 |
| H/I HUM INS 4 mg/L + 0 mg/L DEXTRAN T 2000 | 250 280 | 265 |
| H/I HUM INS 4 mg/L + 1000 mg/L DEXTRAN T 2000 | 250 320 | 300 |
| H/I HUM INS 4 mg/L + 2000 mg/L DEXTRAN T 2000 | 265 300 | 280 |

PASSAGE P15 AFTER THAWING AND P12 IN MEM HT
GROWTH AT 37° C. AND TESTS FOR PRODUCTION AT 35° C.
PLATES
CHANGE OF MEDIUM EVERY 24 HOURS
HUMAN INS ELI LILLY 319KK9B
DEXTRAN T 2000 (PHARMACIA): MW 2,000,000 Da

EXAMPLE 2

Study of the Effects of Sulfated Polymers on the Expression of Factor VIII Delta 2

1) Sulfated dextran

A dose-effect of sulfated dextran (PHARMACIA MW: 500,000) was carried out. Table 2 below also shows the data obtained with the same medium containing two units of recombinant von Willebrand factor.

Under these conditions it is possible, in a production cycle lasting from the 3rd to the 6th day with daily renewal of medium, to obtain, during one of the periods of incubation (5th to 6th day), quantities of factor VIII delta 2, determined by ELISA, which are at most equivalent to ⅔ of the activities accumulated in the presence of two units/ml of recombinant von Willebrand factor.

These activities represent, furthermore, about 2 to 3 times the level of activities obtained in a medium not containing either recombinant von Willebrand factor or sulfated dextran and in the absence of phospholipids.

2) Bovine heparin (KABI VITRUM)

The results of a study of a dose-effect of bovine heparin are summarized in Table 3.

During the first cycles of production, heparin shows a very limited, even non-existent, effect on the expression of factor VIII delta 2. During the last day of incubation D5-D6, a very weak dose-effect relationship can be shown.

TABLE 2

STUDY OF THE EFFECTS OF THE ADDITION OF DEXTRAN SULFATE TO THE PRODUCTION MEDIA FOR FACTOR VIII DELTA 2 CLONE CHO TG 2307-11-3

| PRODUCTION MEDIA | APTT* mU/ML D3–D4 | ELISA mU/ML D3–D4 | APTT* mU/ML D4–D5 | ELISA mU/ML D4–D5 | APTT* mU/ML D5–D6 | ELISA mU/ML D5–D6 |
|---|---|---|---|---|---|---|
| MEM HT 10 FCS ND | 570 608 | — | 11700 9000 | 651 | 720 760 | 15900 16400 |
| H/I HUM INS 4 mg/L + 2 U vWFrec CNTS/ML | 249 280 | | 7300 7500 | 467 409 | 500 510 | 10000 8400 |
| H/I HUM INS 4 mg/L + 250 mg/L DS | ND | 2800 6000 | ND | 2200 1600 | ND | 4200 4500 |
| H/I HUM INS 4 mg/L + 500 mg/L DS | ND | 4500 3100 | ND | 4600 4300 | ND | 4600 4300 |
| H/I HUM INS 4 mg/L + 1000 mg/L DS | ND | 3400 3000 | ND | 4800 4700 | ND | 5000 6400 |
| H/I HUM INS 4 mg/L + 2000 mg/L DS | ND | 3800 3400 | ND | 5000 5000 | ND | 6300 6500 |

APTT is Activated Partial Thromboplastin Time
PASSAGE P24 AFTER THAWING AND P21 IN MEM HT FCS ND 701121
GROWTH AT 37° C. AND TESTS FOR PRODUCTION AT 35° C.
CHANGE OF MEDIUM EVERY 24 HOURS
HUMAN INS ELI LILLY 319KK9B
6-WELL PLATES NUNC
DS: DEXTRAN SULFATE MW: 500,000 PHARMACIA 17% S
ND: CANNOT BE DOSED BECAUSE OF THE ANTICOAGULATING ABILITY OF SULFATE D DEXTRAN

TABLE 3

STUDY OF THE EFFECTS OF THE ADDITION OF BOVINE HEPARIN TO THE PRODUCTION MEDIA FOR FACTOR VIII DELTA 2 CLONE CHO TG 2307-11-3

| PRODUCTION MEDIA | APTT mU/ML D3-D4 | ELISA mU/ML D3-D4 | APTT mU/ML D4-D5 | ELISA mU/ML D4-D5 | APTT mU/ML D5-D6 | ELISA mU/ML D5-D6 |
|---|---|---|---|---|---|---|
| MEM HT 10 FCS ND | 1500 | 18530 | 1920 | 35000 | 5000 | 36000 |
|  | 1570 | 14920 | 2230 | 36000 | 2830 | 27300 |
| H/I HUM INS 4 mg/L + | 900 | 11410 | 1220 | 24400 | 1870 | 28900 |
| 2 U vWFrec CNTS/ML | 1050 | 11400 | 1070 | 29300 | 2100 | 32500 |
| H/I HUM INS 4 mg/L | 213 | 1850 | 130 | 2630 | 142 | 2000 |
|  | 148 | 1460 | 110 | 3050 | 125 | 1100 |
| H/I HUM INS 4 mg/L HEPARIN 10 U/ML | ND | 2060 | ND | 1110 | ND | 800 |
|  |  | 1300 |  | 1560 |  | 1100 |
|  |  | 2950 |  | 1850 |  | 2400 |
| H/I HUM INS 4 mg/L HEPARIN 20 U/ML | ND | 2430 | ND | 1650 | ND | 2400 |
|  |  | 2300 |  | 2060 |  | 3000 |
|  |  | 2480 |  | 1940 |  | 3400 |
| H/I HUM INS 4 mg/L HEPARIN 40 U/ML | ND | 2500 | ND | 2170 | ND | 3500 |
|  |  | 3620 |  | 3220 |  | 5300 |
|  |  | 3120 |  | 2350 |  | 4800 |
| H/I HUM INS 4 mg/L HEPARIN 80 U/ML | ND | 3120 | ND | 2850 | ND | 4000 |
|  |  | 3680 |  | 3400 |  | 5300 |
|  |  | 3920 |  | 3400 |  | 5000 |

PASSAGE P24 AFTER THAWING AND P21 IN MEM HT FCS ND 701121
GROWTH AT 37° C. AND TESTS FOR PRODUCTION AT 35° C.
CHANGE OF MEDIUM EVERY 24 HOURS
HUMAN INS ELI LILLY 319KK9B
BOVINE HEPARIN KABI VITRUM
ND: CANNOT BE DOSED BECAUSE OF THE ANTICOAGULATING ABILITY OF HEPARIN

EXAMPLE 3

The effects of combining sulfated dextran and calcium chloride on the rate of expression of factor VIII delta 2 have also been evaluated, in comparison with control media containing either 10% fetal calf serum, or 2 U/ml von Willebrand factor, or only human insulin which is used in the composition of all the media without serum used in the experiment.

The results obtained are shown in Table 4 below.

It emerges that for the values which are close to the optimum, that is to say 1000 mg/l sulfated dextran and 2 mM calcium chloride (1 mM in minimal medium+1 mM added), it is possible to accumulate in 24 hours between 20 and 21 units of antigen of factor VIII delta 2, in other words, about ⅔ of the quantity accumulated in the presence of 2 units of recombinant von Willebrand factor (2 U/ml) and 6 to 7 times the quantity accumulated in the absence of fetal calf serum or von Willebrand factor.

It is also observed that in the absence of fetal calf serum or recombinant von Willebrand factor, the activities accumulated in 24 hours are never greater than 3 units/ml and are 2.27 units/ml on average, that is to say, very significantly lower than the activities accumulated in the presence of optimum quantities of sulfated dextran.

TABLE 4

STUDY OF THE EFFECTS OF THE ADDITION OF DEXTRAN SULFATE TO THE PRODUCTION MEDIA FOR FACTOR VIII DELTA 2 CLONE CHO TG 2307-11-3
DOEHLERT DEXTRAN SULFATE (0–2000 mg/L)/CaCl₂ (2–11 mM)

| PRODUCTION MEDIA | APTT mU/ML D3-D4 | ELISA mU/ML D3-D4 | APTT mU/ML D4-D5 | ELISA mU/ML D4-D5 | APTT mU/ML D5-D6 | ELISA mU/ML D5-D6 | APTT mU/ML D6-D7 | ELISA mU/ML D6-D7 |
|---|---|---|---|---|---|---|---|---|
| MEM HT 10% FCS ND | 1500 | 18500 | 1920 | 34000 | 2830 | 28000 | 1310 | 30700 |
|  | 1600 | 14900 | 2230 | 35000 | 5000 | 36000 | 1850 | 35000 |
| H/I HUM INS 4 mg/L + | 1050 | 11400 | 1220 | 24400 | 1870 | 28900 | 1750 | 33700 |
| 2 U vWFrec CNTS/ML | 900 | 11400 | 1070 | 29300 | 2100 | 32500 | 1370 | 26700 |
| H/I HUM INS 4 mg/L | 210 | 1850 | 130 | 2650 | 125 | 1130 | 142 | 3000 |
|  | 150 | 1460 | 110 | 3050 | 142 | 1900 | 124 | 3170 |
| *H/I HUM INS 4 mg/L + 1000 mg/L DS Ca 5 mM | ND | 856 | ND | 8000 | ND | 5000 | ND | 5700 |
| H/I HUM INS 4 mg/L + 1000 mg/L DS Ca 10 mM | ND | 980 | ND | 6150 | ND | 4700 | ND | 3920 |
|  |  |  |  |  |  | 6000 |  | 4980 |
| H/I HUM INS 4 mg/L + 1000 mg/L DS Ca 1 mM | ND | 1350 | ND | 8400 | ND | — | ND | 21610 |
|  |  |  |  |  |  | — |  | 20550 |
| H/I HUM INS 4 mg/L + 1866 mg/L DB Ca 7.5 mM | ND | 1380 | ND | 8550 | ND | 10700 | ND | 12000 |
|  |  |  |  |  |  | 8000 |  | 10520 |
| H/I HUM INS 4 mg/L + 134 mg/L DS Ca 2.5 mM | ND | 655 | ND | 6600 | ND | 9900 | ND | 15585 |
|  |  |  |  |  |  | 10150 |  | 15410 |
| H/I HUM INS 4 mg/L + 134 mg/L DS Ca 7.5 nM | ND | 250 | ND | 6700 | ND | 7800 | ND | 11260 |
|  |  |  |  |  |  | 10150 |  | 13900 |
| H/I HUM INS 4 mg/L + 1866 mg/L DS | ND | 1420 | ND | 6300 | ND | 9700 | ND | 15510 |
|  |  |  |  |  |  | 10950 |  | 14120 |

TABLE 4-continued

STUDY OF THE EFFECTS OF THE ADDITION OF DEXTRAN SULFATE
TO THE PRODUCTION MEDIA FOR FACTOR VIII DELTA 2 CLONE CHO TG 2307-11-3
DOEHLERT DEXTRAN SULFATE (0-2000 mg/L)/CaCl$_2$ (2-11 mM)

| PRODUCTION MEDIA | APTT mU/ML D3-D4 | ELISA mU/ML D3-D4 | APTT mU/ML D4-D5 | ELISA mU/ML D4-D5 | APTT mU/ML D5-D6 | ELISA mU/ML D5-D6 | APTT mU/ML D6-D7 | ELISA mU/ML D6-D7 |
|---|---|---|---|---|---|---|---|---|
| Ca 2.5 mM | | | | | | | | |

PASSAGE P24 AFTER THAWING AND P21 IN MEM HT FCS ND 701121
GROWTH AT 37° C. AND TESTS FOR PRODUCTION AT 35° C.
CHANGE OF MEDIUM EVERY 24 HOURS
HUMAN INS ELI LILLY 319KK9B
6-WELL PLATES NUNC
DS: DEXTRAN SULFATE MW: 500,000 PHARMACIA 17% S
*: AVERAGE FOR 6 WELLS (BO) AVERAGE FOR 2 WELLS FOR OTHER VALUES
ELISA D3-D4 CARRIED OUT 24 H AFTER SAMPLING
ND: CANNOT BE DOSED BECAUSE OF THE ANTICOAGULATING ABILITY OF SULFATE D DEXTRAN

TABLE 5

STUDY OF THE EFFECTS OF THE ADDITION OF SULFATED POLYMERS
TO THE PRODUCTION MEDIA FOR FACTOR VIII DELTA 2 CLONE CHO TG 2307-11-3
EFFECTS OF HYDROXYETHYLSTARCH SULFATES OF MW 200,000 Da AT 3.76% AND 13.1% OF S
AND OF SIGMA LOW VISCOSITY CARBOXYMETHYLCELLULOSE

| PRODUCTION MEDIA | APTT mU/ML D3-D4 | ELISA mU/ML D3-D4 | APTT mU/ML D4-D5 | ELISA mU/ML D4-D5 | APTT mU/ML D5-D6 | ELISA mU/ML D5-D6 | APTT mU/ML D6-D7 | ELISA mU/ML D6-D7 |
|---|---|---|---|---|---|---|---|---|
| MEM HT 10% FCS ND | 3100 | 40200 | 1370 | 20000 | 740 | 18500 | 810 | 13500 |
| H/I HUM INS 4 mg/L + 2 U vWFrec CNTS/ML | 1300 | 18200 | 1530 | 30800 | 940 | 22400 | 1600 | 21000 |
| H/I HUM INS 4 mg/L | 170 | 3200 | 124 | 1100 | 25 | 760 | 260 | 1900 |
| H/I HUM INS 4 mg/L + 100 mg/L CMC | ND | 5500 | ND | 1400 | ND | 970 | ND | 1820 |
| H/I HUM INS 4 mg/L + 500 mg/L CMC | ND | 4600 | ND | 1900 | ND | 850 | ND | 2100 |
| H/I HUM INS 4 mg/L + 1000 mg/L CMC | ND | 4400 | ND | 2200 | ND | 1200 | ND | 2350 |
| H/I HUM INS 4 mg/L + 100 mg/L-HESS 13.1% | ND | 8700 | ND | 10300 | ND | 5800 | ND | 5700 |
| H/I HUM INS 4 mg/L + 500 mg/L-HESS 13.1% | ND | 12800 | ND | 21900 | ND | 9900 | ND | 10500 |
| H/I HUM INS 4 mg/L + 1000 mg/L-HESS 13.1% | ND | 11900 | ND | 18000 | ND | 11500 | ND | 12800 |
| H/I HUM INS 4 mg/L + 100 mg/L-HESS 3.76% | ND | 7500 | ND | 4900 | ND | 2100 | ND | 2240 |
| H/I HUM INS 4 mg/L + 500 mg/L-HESS 3.76% | ND | 8300 | ND | 11000 | ND | 5000 | ND | 4740 |
| H/I HUM INS 4 mg/L + 1000 mg/L-HESS 3.76% | ND | 8200 | ND | 14200 | ND | 6700 | ND | 5530 |

PASSAGE P19 AFTER THAWING AND P18 IN MEM HT FCS ND 701121
GROWTH AT 37° C. AND TESTS FOR PRODUCTION AT 35° C.
CHANGE OF MEDIUM EVERY 24 HOURS
HUMAN INS ELI LILLY 319KK9B
6-WELL PLATES NUNC
HYDROXYETHYLSTARCH SULFATE MW: 200,000 PFEIFER AND LANGEN 3.76 AND 13.1% S
CONCENTRATED vWFrec CNTS AT 63.7 U/ML OF 11/12/89
ND: CANNOT BE DOSED BECAUSE OF THE ANTICOAGULATING ABILITY OF SULFATED POLYMERS
ELISA OF D4-D5: INCUBATION Ag 14 HOURS AT +20° C.

EXAMPLE 4

Other polymers and in particular, carboxymethylcellulose, hydroxyethylstarch sulfate (MW: 200,000) with 3.76 and 13.1% of sulfur were evaluated for their ability to influence the rate of expression of factor VIII delta 2 in a medium without serum and without factor von Willebrand and this was done relative to controls containing 10% bovine serum, 2 units/ml recombinant von Willebrand factor or neither serum nor von Willebrand. (Table 5)

The carboxymethylcellulose at the concentrations tested does not have a marked effect on the expression of factor VIII delta 2, whereas starch hydroxyethyl sulfate with 13% sulfur at concentrations of 0.5 and 1.0 g/l allows the accumulation in 24 hours of up to about 20 units of C: Ag/ml of factor VIII delta 2, that is to say about ⅔ of what is obtained during the same period in the presence of 2 units/ml of recombinant von Willebrand factor. The same polymer containing only 3.76% of sulfur has an effect on the expression of factor VIII delta 2 which is significantly less marked. This experiment confirms the usefulness of sulfated polysaccharides and reveals the importance of the degree of sulfation in the interaction of polymers with the molecule of factor VIII delta 2.

EXAMPLE 5

Study of the Effects of Sulfated Dextran on the Expression of Factor VIII

The study is carried out using the clone CHO TG 1566-3013 which expresses the molecule of complete factor VIII.

FIG. 1 shows the existence of a dose-effect of sulfated dextran (Pharmacia MW: 500,000) on the expression of factor VIII in 6-well plates.

It is observed that over 2 days of production, D4-D5 and D5-D6, the production of factor VIII is significantly increased relative to a control without sulfated dextran. A threshold is reached at 500 mg/l of sulfated dextran.

EXAMPLE 6

Comparison of the Effects of vWF and Sulfated Dextran (MW: 50,000) on the Expression of Factor VIII in a Chemically Defined Medium This study is carried out in a 1 l bioreactor (SGI). The clone CHO TG 1566-3013 which expresses the complete factor VIII is cultured on the support Cultispher-G at the concentration of 4 g/l (microporous beads of crosslinked bovine gelatin).

After a growth phase of 9 days in an Iscove medium containing 5% FCS, the influence of 3 different production media are serially tested:

- a medium containing 5% FCS and containing neither vWF nor sulfated dextran (medium A)
- a medium without FCS containing 1 UI vWF/ml (medium B)
- a medium without vWF or FCS and containing 200 mg/l sulfated dextran (MW: 50,000) (medium C).

Figure 2:
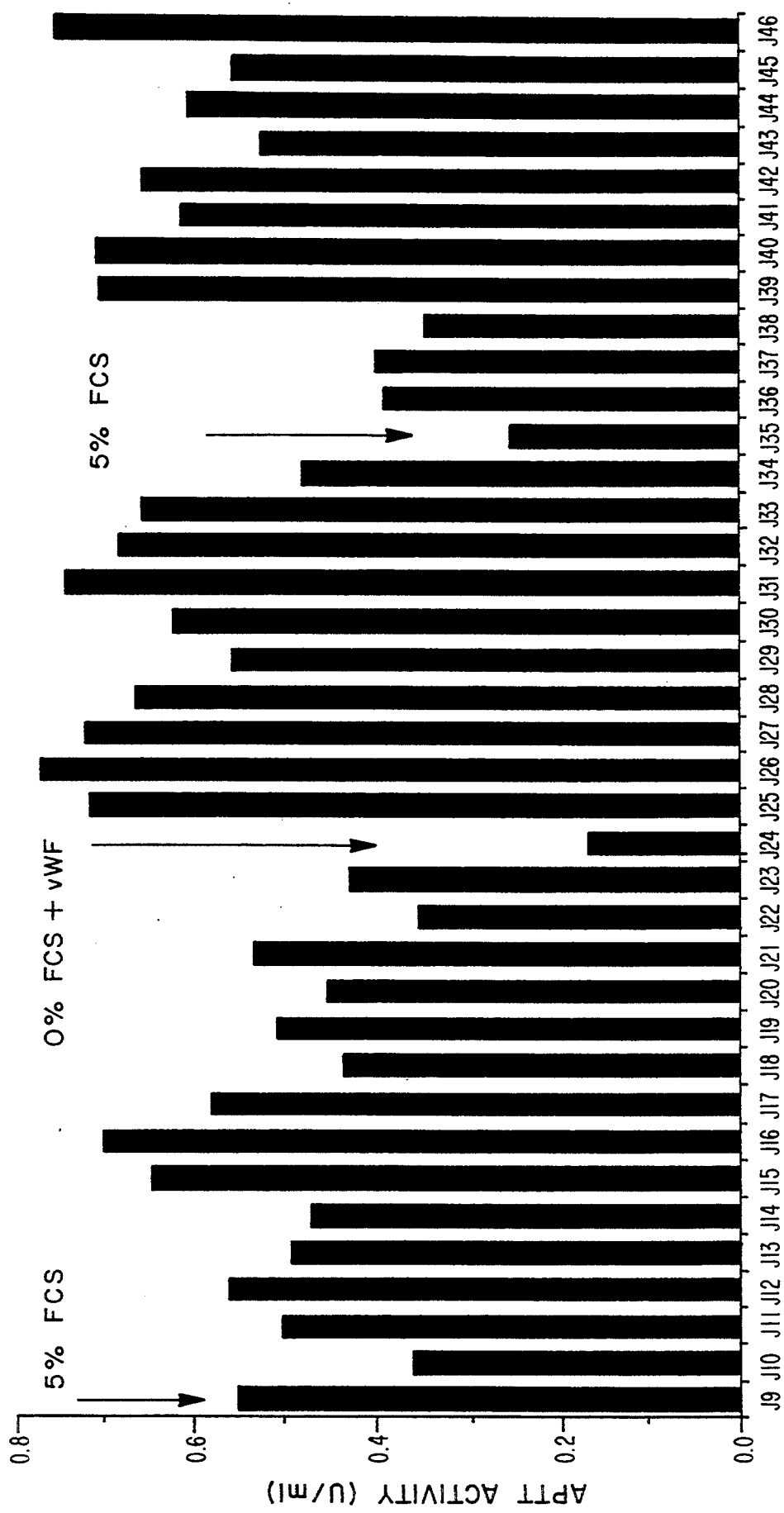
FIG. 2 shows factor VIII expression for cells cultured on medium with 5% FCS, 0% FCS+1 UI vWF per ml, or 0% FCS+200 mg/l sulfated dextran (MW: 50,000).

The results are presented in FIG. 2.

The activity for factor VIII is expressed in units APTT/l (Activated Partial Thromboplastin Time) of medium when a medium which does not contain sulfated dextran, and in the unit Cag (Coagulatoin Antigen) when a medium which contains sulfated dextran (ELISA assay). The ratio between the assays APTT and ELISA is of the order of 1.2 to 1.4 and the Cag units for the DS treated cells have been converted to APTT units for FIG. 2.

It is found that the productions achieved in medium B are higher than those achieved in medium A (680±67 U APTT/l against 502±96 U APTT/l). The productions achieved in medium C are comparable to those obtained in medium B.

In conclusion, it is clearly shown that sulfated dextran can be substituted for von Willebrand factor in order to increase the expression of factor VIII in a chemically defined medium.

We claim:

1. In a process for the preparation and separation of factor VIII or an analog of factor VIII, the process comprising culturing eukaryotic cells which produce and secrete said factor VIII or analog of factor VIII, said eukaryotic cells having incorporated an expression vector containing a gene encoding for said factor VIII or analog of factor VII said cells being chosen among recombinant Veto, Hela, WI38, BHK, CHO, COS-7 and MDCK cells which express the molecule of factor VIII or analog of factor VII in a continuous manner, and then separating said factor VIII or analog of factor VIII wherein the improvement comprises culturing the cells in a serum free culture medium supplemented with at least one derivative which is a sulfated polysaccharide selected from the group consisting of heparin, sulfated dextran and hydroxyethylstarch sulfate of molecular weight between 5,000 and 700,000 and a degree of sulfation of 0.5 to 18% by weight of sulfur in an mount sufficient to provide an enhancement of factor VIII or analog of factor VIII production compared with culturing the cells in a medium without said sulfated polysaccharide.

2. The process of claim 1 wherein the degree of sulfation is in the range of 10 to 18% by weight of sulfur.

3. The process of claim 1 wherein said sulfated polysaccharide is sulfated dextran.

4. In process for the preparation and separation of Factor VIII or an analog of factor VIII, comprising the steps of culturing eukaryotic cells which produce and secrete said factor VIII or analog of factor VIII, said cells, having incorporated an expression vector containing a gene encoding for said factor VIII or analog of factor VIII, said cells being CHO cells which express the molecule of factor VIII or analog of factor VIII in a continuous manner and then separating the factor VIII or analog of factor VIII produced by said cells, wherein the improvement comprises culturing the cells in serum free culture medium supplemented with at least one derivative which is sulfated dextran which has a molecular weight comprised between 5,000 and 700,000 and a degree of sulfation of 10% to 18% by weight of sulfur in an amount sufficient to provide an enhancement of factor VIII or analog of factor VIII production compared with culturing the cells in a medium without said sulfated dextran.

* * * * *

UNITED STATES PATENT AND TRADEMARK OFFICE
CERTIFICATE OF CORRECTION

PATENT NO. : 5,422,250
DATED : June 6, 1995
INVENTOR(S) : Mignot et al.

It is certified that error appears in the above-indentified patent and that said Letters Patent is hereby corrected as shown below:

[57] ABSTRACT, third line, change "a Culture medium" to
--a culture medium--;

In Claim 1, column 16 at line 7 change "factor VII said" to
--factor VIII said--; at line 8 change "Veto" to --Vero--;
at line 9 change "the .molecule" to --the molecule--;
at line 10 change "of factor VII in" to --of factor VIII in--;
at line 18 change "in an mount" to --in an amount--.

Signed and Sealed this

Fifth Day of March, 1996

Attest:

BRUCE LEHMAN

Attesting Officer        Commissioner of Patents and Trademarks